United States Patent
Sun et al.

(10) Patent No.: US 12,032,125 B2
(45) Date of Patent: Jul. 9, 2024

(54) PROTECTIVE TRANSPARENT COATING FOR OPTICAL FILTERS

(71) Applicant: Gentex Corporation, Simpson, PA (US)

(72) Inventors: Xiaodong Sun, Abington Township, PA (US); May L. Castro, Simpson, PA (US)

(73) Assignee: GENTEX CORPORATION, Simpson, PA (US)

( * ) Notice: Subject to any disclaimer, the term of this patent is extended or adjusted under 35 U.S.C. 154(b) by 895 days.

(21) Appl. No.: 16/971,864

(22) PCT Filed: Feb. 21, 2019

(86) PCT No.: PCT/US2019/018991
§ 371 (c)(1),
(2) Date: Aug. 21, 2020

(87) PCT Pub. No.: WO2019/165098
PCT Pub. Date: Aug. 29, 2019

(65) Prior Publication Data
US 2021/0011203 A1 Jan. 14, 2021

Related U.S. Application Data

(60) Provisional application No. 62/634,743, filed on Feb. 23, 2018.

(51) Int. Cl.
G02B 1/14 (2015.01)
A61F 9/02 (2006.01)
G02B 5/28 (2006.01)
G02C 7/10 (2006.01)

(52) U.S. Cl.
CPC ............... *G02B 1/14* (2015.01); *A61F 9/022* (2013.01); *G02B 5/285* (2013.01); *G02C 7/107* (2013.01); *G02C 2202/16* (2013.01)

(58) Field of Classification Search
CPC . G02B 1/14; G02B 5/285; A61F 9/022; A61F 9/065; G02C 7/107; G02C 2202/16
See application file for complete search history.

(56) References Cited

U.S. PATENT DOCUMENTS

| | | | |
|---|---|---|---|
| 5,910,375 | A | 6/1999 | Parker et al. |
| 6,007,569 | A | 12/1999 | Frenkel et al. |
| 2002/0136899 | A1 | 9/2002 | Derojas et al. |
| 2003/0179459 | A1 | 9/2003 | Hayashi |
| 2005/0008774 | A1 | 1/2005 | Borgharkar et al. |
| 2007/0141243 | A1 | 6/2007 | Bell |

(Continued)

OTHER PUBLICATIONS

International Search Report dated Apr. 24, 2019 for International Patent Application No. PCT/US2019/018991, 2 pages.

(Continued)

*Primary Examiner* — James C. Jones
(74) *Attorney, Agent, or Firm* — Morgan, Lewis & Bockius LLP

(57) ABSTRACT

An optically transparent device includes an exterior lens and an optical filter coupled to an inner surface of the exterior lens. A protective coating comprised of an acrylate may be coupled to an inner surface of the optical filter to reduce fragments of the optical filter from detaching from the exterior lens.

9 Claims, 5 Drawing Sheets

(56) References Cited

U.S. PATENT DOCUMENTS

| | | | |
|---|---|---|---|
| 2007/0179224 A1* | 8/2007 | Fanayar | G02B 1/105 |
| | | | 524/100 |
| 2007/0298242 A1 | 12/2007 | Huo | |
| 2012/0021135 A1* | 1/2012 | Yajima | B29D 11/00644 |
| | | | 427/163.1 |
| 2015/0234208 A1 | 8/2015 | De Ayguavives et al. | |

OTHER PUBLICATIONS

Written Opinion dated Apr. 24, 2019 for International Patent Application No. PCT/US2019/018991, 7 pages.

\* cited by examiner

PROTECTIVE TRANSPARENT COATING FOR OPTICAL FILTERS

CROSS REFERENCE TO RELATED APPLICATIONS

This application is a U.S. National Phase of International Application No. PCT/US2019/018991 filed on Feb. 21, 2019, which claims the benefit of U.S. Provisional Patent Application No. 62/634,743 filed Feb. 23, 2018 entitled "Protective Transparent Coating for Optical Filters", each of which is incorporated by reference herein in its entirety.

FIELD OF THE INVENTION

The present application generally relates to transparent, protective coatings for optical filters and methods of preparing the same.

BRIEF SUMMARY OF THE INVENTION

In one embodiment, there is an optically transparent device comprising: an exterior lens; and an optical filter coupled to an inner surface of the exterior lens; and a protective coating coupled to an inner surface of the optical filter, the protective coating being comprised of acrylate. In one embodiment, the protective coating is comprised of urethane acrylate. In one embodiment, the protective coating is comprised of aliphatic urethane acrylate. In one embodiment, the protective coating is comprised of elastomeric urethane acrylate. In one embodiment, the protective coating contains one or more flow additives. In one embodiment, the one or more flow additives may include non-ionic, dimethysiloxane and/or silicone containing surface additives. In one embodiment, the protective coating contains a solvent or mixture of solvents. In one embodiment, the optical filter is comprised of a multilayer, dielectric coating. In one embodiment, the protective coating is a radiation curable coating. In one embodiment, the protective coating contains a photo-initiator. In one embodiment, the protective coating contains one or more electromagnetic wave management materials. In one embodiment, the protective coating includes nanoparticles. In one embodiment, the exterior lens is a spectacle lens, shield, mask, goggle, visor, sheet, window, or cover plate. In one embodiment, the protective coating includes one or more filtering materials configured to limit the transmission of a laser light through the optically transparent device. In one embodiment, the protective coating includes one or more filtering materials configured to control the transmission of specific electromagnetic wavelength bands. In one embodiment, the protective coating is comprised of two or more layers. In one embodiment, the protective coating comprises approximately 20% to approximately 80% acrylate by weight of a coating formulation. In one embodiment, the protective coating is comprised of multifunctional acrylate. In one embodiment, a thickness of the protective coating is between approximately 2 microns and approximately 100 microns. In one embodiment, an anti-reflective, anti-fog, anti-soil, hydrophilic, hydrophobic and/or scratch resistant coating is coupled to the protective coating.

In one embodiment, there is an optically transparent device comprising: an exterior lens comprised of: a concave surface configured to face toward a user, and a convex surface configured to face away from a user, each of the concave and convex surfaces being coated with an abrasion resistant coating; and a dielectric optical filter coupled to the concave surface; an adhesion primer coupled to the dielectric optical filter; a protective acrylate coating coupled to the adhesion primer wherein the protective acrylate coating has a thickness of approximately 5 microns to approximately 50 microns; and an anti-reflective and/or anti-fog coating coupled to the protective acrylate coating. In one embodiment, the protective acrylate coating is comprised of approximately 20% to approximately 80% of acrylate by weight of the coating formulation, and further comprises: a photo-initiator; a solvent mixture comprised of one or more solvents comprising: approximately 20% to approximately 80% by weight of the coating formulation; one or more flow additives comprised of: non-ionic, dimethysiloxane and/or silicone containing surface additives; wherein the one or more flow additives are between approximately 0.01% to approximately 3% by weight of the protective acrylate coating formulation, wherein the thickness of the protective acrylate coating is between approximately 2 microns to approximately 100 microns.

In one embodiment, there is a method for manufacturing an optically transparent device comprising the steps of: providing an optically transparent substrate; coupling an optical filter to the optically transparent substrate; applying a protective coating to the optical filter; and curing the protective coating by radiation. In one embodiment, applying a primer layer to a lint free, dry cloth and then wiping the primer layer onto the optical filter. In one embodiment, applying a primer layer onto the optical filter by flowing, spinning, dipping and/or spray coating methods to form a primed optical filter. In one embodiment, drying the primer layer before applying the protective coating to the optical filter. In one embodiment, applying the protective coating to the optical filter includes flowing, spinning, dipping and/or spraying the coating onto the optical filter. In one embodiment, applying an anti-reflective, anti-fog, anti-soil, hydrophilic, hydrophobic and/or scratch resistant coating to the protective coating. In one embodiment, curing the protective coating includes the use of ultraviolet radiation. In one embodiment, coupling the optical filter to the optically transparent substrate includes applying the optical filter using vacuum deposition technology. In one embodiment, the optical filter is preformed to the general shape of the optically transparent substrate and subsequently bonded to the optically transparent substrate.

BRIEF DESCRIPTION OF THE SEVERAL VIEWS OF THE DRAWINGS

The foregoing summary, as well as the following detailed description of embodiments of the protective transparent coating for optical filters, will be better understood when read in conjunction with the appended drawings of exemplary embodiments. It should be understood, however, that the invention is not limited to the precise arrangements and instrumentalities shown.

In the drawings.

DETAILED DESCRIPTION OF THE INVENTION

Certain advanced laser eye protection ("LEP") devices such as visors, goggles, spectacles, shields, masks, certain windows and cover plates for optical sensors, vision systems etc., utilize optical filters that are often constructed of brittle, multilayer coatings. These coatings may be glass like and if exposed to impact, either directly, or indirectly by impact on the opposite side of the device ("exterior" as referred to herein), may shatter and separate the optical filter from the interior of the device creating an eye hazard for the user or cause damage to an instrument. Traditionally, protecting an optical filter and/or protecting a user from a damaged optical filter may be achieved through encapsulating the optical filter by bonding a conformal cover plate to the otherwise exposed side of the optical filter to sandwich the optical filter. However, doing so may add thickness and weight to the device which may be undesirable for the wearer. Additionally, the bonding process used to attach the cover plate to the optical filter may increase costs and negatively affect system optics if the cover plate does not accurately match the curvature or shape of the underlying lens.

The present invention generally relates to a transparent, protective coating and, more particularly, to a coating suitable to restrain the release of particles or fragments from a transparent article with a sub-surface that can spall, shatter or otherwise disengage from the lens substrate on impact. As is described below, in some embodiments, a radiation cured acrylate or mixture of acrylates coating has been developed.

Figure 1A:
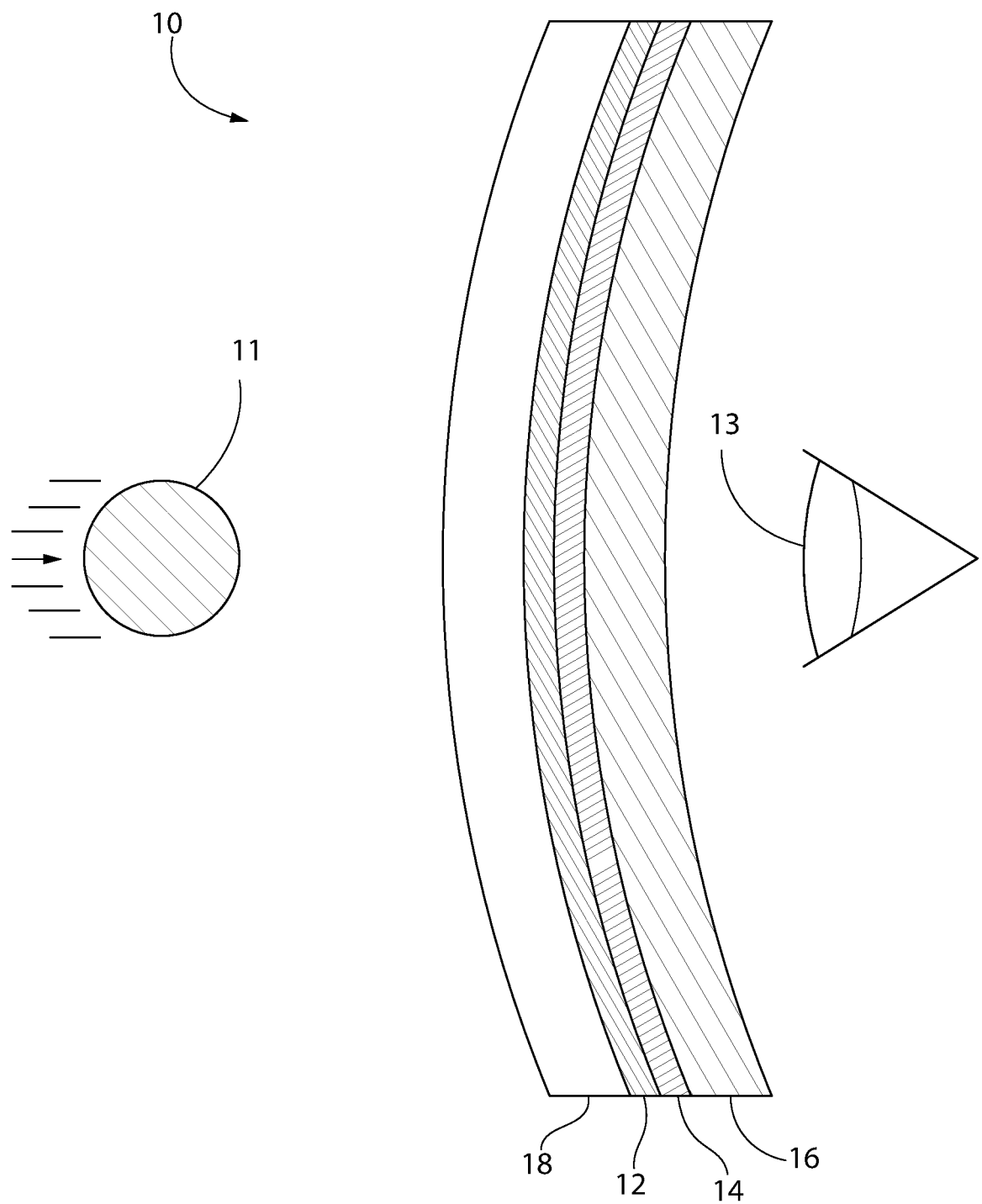
FIG. 1A is an enlarged partial side cross sectional view of an optically transparent lens having an optical filter and protective layer as known in the art.
Figure 1B:
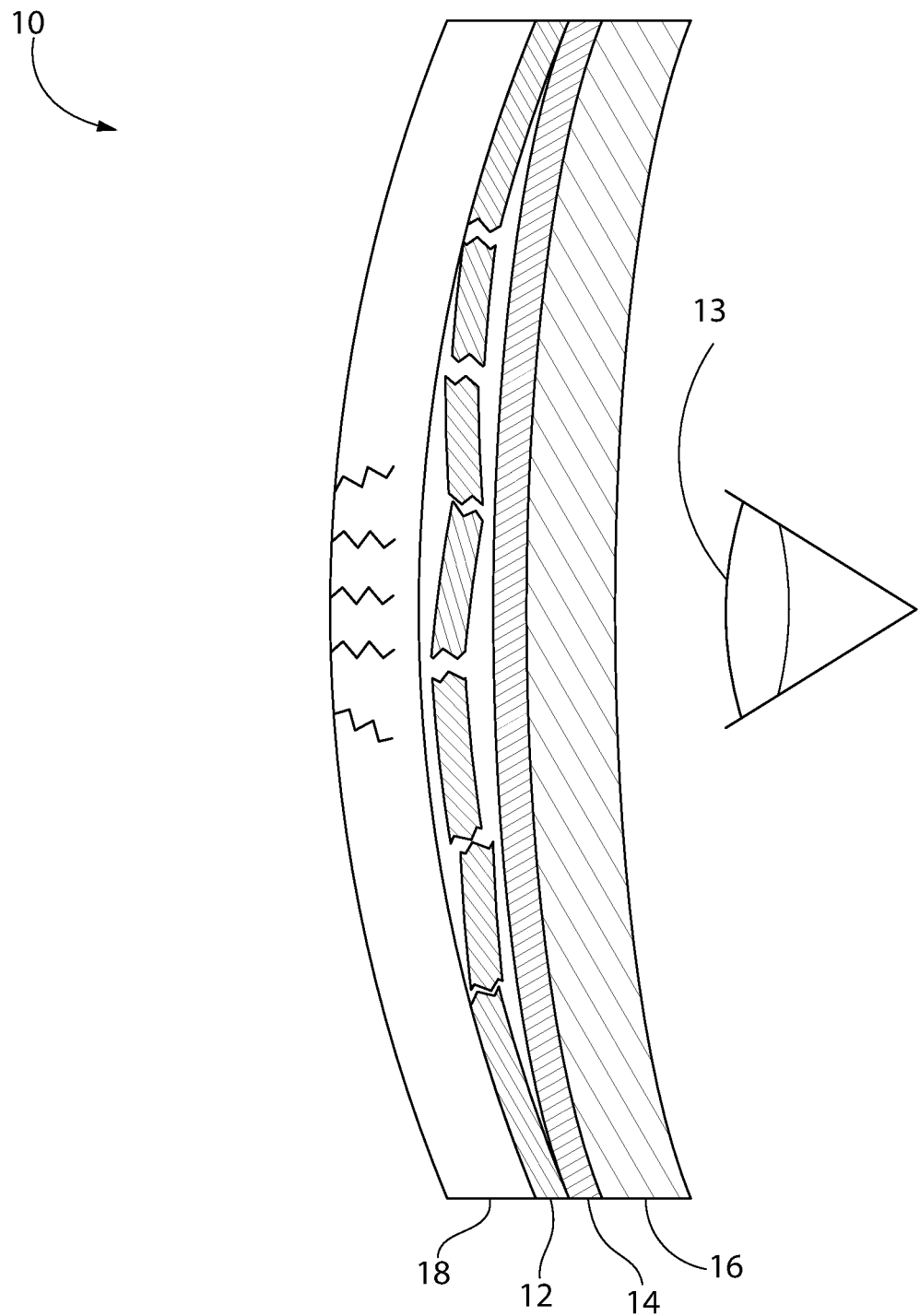
FIG. 1B is an enlarged partial side cross sectional view of an optically transparent lens, upon impact, having an optical filter and protective layer, as known in the art.

Referring to FIGS. 1A and 1B, there is shown a traditional approach to optical filter protection (for example laser eye protection ("LEP")). A transparent article 10 includes an exterior lens 18, an optical filter 12 coupled to the exterior lens 18, with an adhesive 14 applied over the optical filter 12 and coupled to an interior lens 16. Advanced LEP devices such as this may incorporate a brittle optical filter 12. As mentioned above, due to the sensitive nature, such a filter would need to be protected from environmental factors and from harming the user 13 in the event of a high-velocity impact. For example, a projectile 11 (see FIG. 1A) may strike the exterior surface of exterior lens 18 causing the optical filter 12 to crack (see FIG. 1B). An interior lens 16 may be provided over the optical filter 12 to prevent fragments dislodging from the cracked optical filter 12 toward the user's eye, but such a protective lens 16 is unduly thick and heavy.

Figure 2:
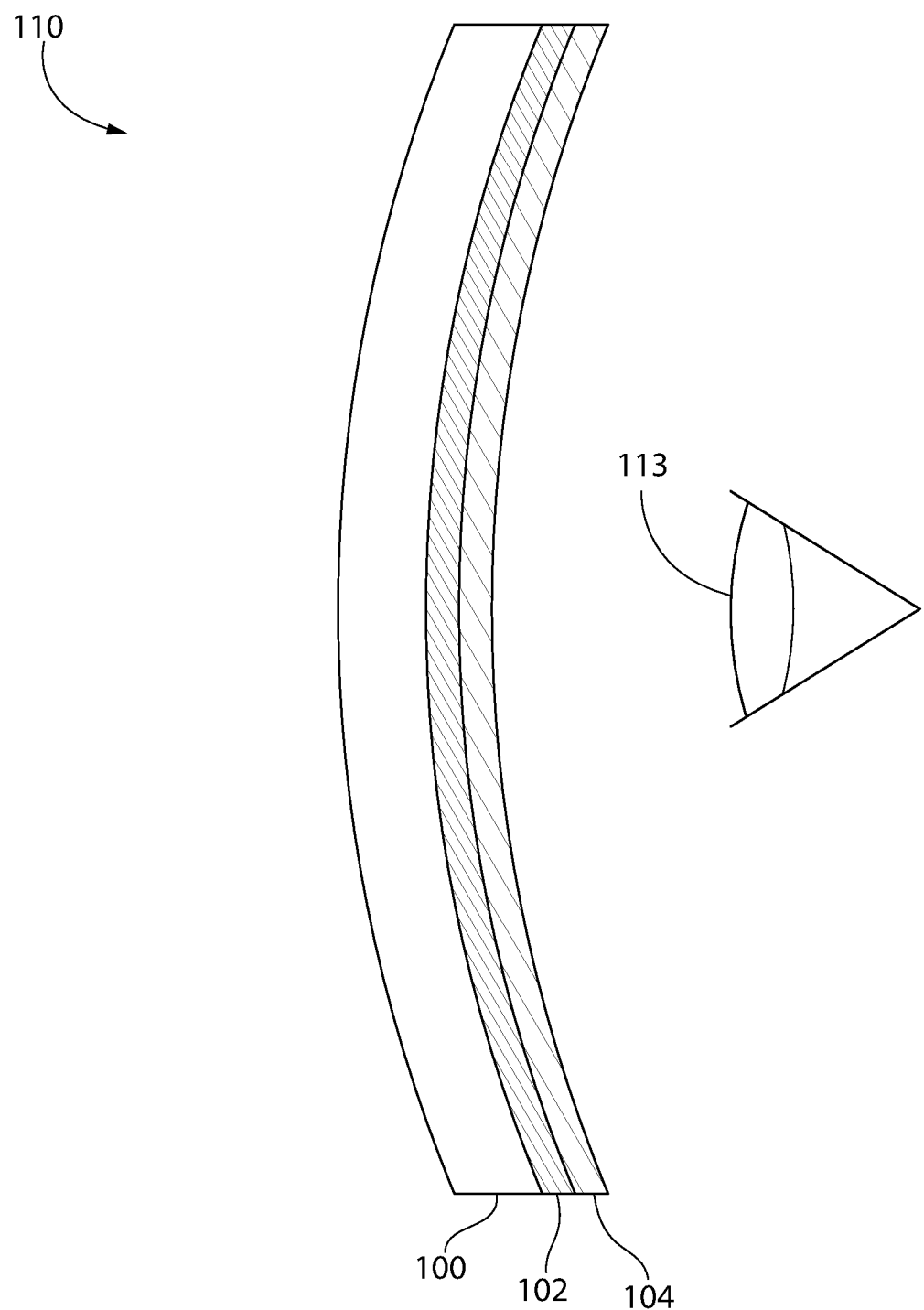
FIG. 2 is an enlarged partial side cross sectional view of an optically transparent lens having an optical filter and a protective coating layer in accordance with an exemplary embodiment of the present invention.

Referring to FIG. 2, a first exemplary embodiment of the present invention is shown. In one embodiment there is an optically transparent device 110 which includes an exterior lens 100, an optical filter 102 coupled to an inner surface of the exterior lens 100, and a protective coating 104 coupled to an inner surface of the optical filter 102. In one embodiment, optically transparent device 110 does not include an interior lens. In one embodiment, optically transparent device includes a single lens 100. In one embodiment, optical filter 102 is not positioned between two lenses. In some embodiments, optical filter 102 is situated between and is in direct contact with the inner surface of the exterior lens 100. In one embodiment, an inner surface of the protective coating 104 is not coupled to a further layer or substrate.

In one embodiment, exterior lens 100 is shaped for use in or as spectacles, shields, lenses, goggles, visors, windows and/or optical sensor covers. Exterior lens 100 may have any desirable shape, size and thickness. Exterior lens 100 may have one or more convex or concave side surfaces. In one embodiment, the optical filter 102 is positioned on the inner, concave side surface of the exterior lens 100. In some embodiments, exterior lens 100 has one or more flat side surfaces. Exterior lens 100 may have an optical power. In other embodiments, exterior lens 100 has zero optical power.

In some embodiments, exterior lens 100 is comprised of a transparent polymer. In one embodiment, exterior lens 100 is comprised of a thermoset material. In one embodiment, the thermoset material is selected from the group that may include polymers of diethylene glycol bis (allyl carbonate) and diallyl diglycol carbonate and a combination thereof. In one embodiment, the thermoset material is selected from the group that may include polymers of 1,3 butylene glycol dimethacrylate, acrylonitrile, urethanes, allyl methacrylate, ethoxymethyl methacrylate, ethylene glycol dimethacrylate, polyethylene glycol dimethacrylate, allyl esters, co-polymers of allyl esters with styrene or vinyl type monomers and combinations thereof. In some embodiments, exterior lens 100 comprises a thermoplastic material. In one embodiment, the thermoplastic material is selected from the group including polysulfones, polyethersulfones, polyamides, polystyrenes, polymethylmetacrylate, polyolefins, polyurethanes, polyesters, polycarbonates and/or mixtures of polycarbonate and polysiloxanes, polyurethanes, polystyrenes, polysulfones, polyesters, acrylics and combinations thereof. In some embodiments, exterior lens 100 comprises a high refractive index material. In one embodiment, the high refractive index material is selected from the group including poly-thio-urethanes and high refractive index copolymers of urethanes, sulfur-containing aromatic vinyl compounds and bromine-containing aromatic acrylic compounds and combinations thereof.

An optical filter 102 is coupled to the inner surface (e.g., facing user) of the exterior lens 100. An LEP lens may incorporate a dielectric optical filter approximately 20 microns in thickness, for example, which may be constructed from multiple thin layers of dielectric metal oxides and applied via vacuum deposition onto an optical substrate, such as a polycarbonate lens. In one embodiment, the optical filter 102 is a thin film comprised of dielectric materials. Optical filter 102 may be comprised of multiple layers of dielectric materials. In some embodiments, optical filter 102 is comprised of multiple layers of dielectric materials in combination with metallic layers. Dielectric coatings may be comprised of transparent dielectric materials and may be used for selective filtering of electromagnetic waves, laser mirrors and/or anti-reflection. Dielectric coatings, also called thin film coatings or interference coatings, may include thin (e.g., sub-micron) layers of transparent dielectric materials, which are deposited on exterior lens 100. Optical filter 102 may essentially modify the reflective properties of the optical filter 102 by exploiting the interference of reflections from multiple optical interfaces. Optical filter 102 may be used for highly reflecting laser mirrors (e.g., to protect a user 113 from damage to their eyes from lasers) or partially transmissive output couplers, for dichroic mirrors (treating different wavelengths differently), for anti-reflection coatings, for various kinds of optical filters (e.g., for attenuation of certain wavelength regions), and thin-film polarizers. Optical filter 102 may include one or more (e.g., over a hundred) of thin-film layers. Optical filter 102 may include discrete layers with different refractive indices than one another. In other embodiments, optical filter 102 may include a gradient-index coating, such as a rugate filter, where the refractive index is varied continuously through a layer. In one embodiment, the melting point of optical filter 102 is different from the melting point of the exterior lens 100. In one embodiment, optical filter 102 has a coefficient of thermal expansion that is different from the coefficient of thermal expansion of the exterior lens 100. In one embodiment, optical filter 102 is comprised of glass. In some embodiments, optical filter 102 is comprised of metal, semi-conductor and/or polymeric material. In some embodiments, optical filter 102 includes at least one metal layer. Optical filter 102 may include one or more metal oxides and/or metal fluorides. In one embodiment, optical filter 102 includes one or more layers of $TiO_2$, $SiO_2$, $Al_2O_3$, $Ta_2O_5$, $MgF_2$, $LaF_3$ and/or $AlF_3$. In one embodiment, optical filter 102 has one or more layers having a refractive index of approximately 1.3 to approximately 3.0. Optical filter 102 may be comprised of any preferred material or combination of materials with the desired optical filter properties.

One or both side surfaces of exterior lens 100 may include an optical filter 102. In one embodiment, only a portion of the exterior lens 100 is coupled to optical filter 102. In one embodiment, optical filter 102 is intended to face a user's 113 eye or sensor. In other embodiments, optical filter 102 is intended to face away from the user's 113 eye or sensor. In some embodiments, optical filter 102 includes a plurality of layers. In one embodiment, at least one layer of the plurality of layers of optical filter 102 layers has the same composition as at least one other coating layer. In some embodiments, at least one layer of the optical filter 102 has a different composition than at least one other layer of optical filter 102. The optical filter 102 may have a thickness of 1 micron to 100 microns. The optical filter 102 may have a thickness greater than 100 microns. In some embodiments, optical filter 102 is pre-formed and bonded to the optically transparent device 110. In other embodiments, optical filter 102 is deposited on the exterior lens 100 by vacuum coating.

In one embodiment, the protective coating 104 retains the optical filter 102 upon impact to the device which would otherwise cause the optical filter 102 to detach from lens 100. In one embodiment, the protective coating 104 is flexible. In one embodiment, the protective coating 104 is applied to and covers the optical filter 102. In one embodiment, the protective coating 104 covers substantially all of the inner surface of the optical filter 102. In other embodiments, the protective coating 104 only covers a desired portion of the optical filter 102. As discussed in further detail below, the protective coating 104 may be a radiation curable coating. A thickness of the protective coating 104 may be between approximately 2 microns to approximately 100 microns. In one embodiment, a thickness of the protective coating 204 is between approximately 5 microns to approximately 50 microns.

In one embodiment, the thickness of the protective coating 104 is between approximately 7 microns to approximately 10 microns. In another embodiment, the thickness of the protective coating 104 is between approximately 20 microns to approximately 50 microns. The design thickness of the protective coating 104 may be a function of the final service requirement, in which the higher the energy impact service requirement may be, the thicker the protective coating system may be. The protective coating 104 may be comprised of a single layer or multiple layers of the same material or different materials. Each layer may have a thickness between approximately 1 micron to approximately 10 microns. Each layer may have a thickness greater than approximately 11 microns. In one embodiment, the protective coating 104 is comprised of 1 layer. In another embodiment, the protective coating 104 is comprised of 2 layers. In some embodiments, the protective coating 104 is comprised of 3 layers. In another embodiment, the protective coating 104 is comprised of 4 layers. In one embodiment, the protective coating 104 is comprised of 5 layers. In another embodiment, the protective coating 104 is comprised of 6 layers. In some embodiments, the protective coating 104 is comprised of 7 layers. In one embodiment, the protective coating 104 is comprised of 8 layers. In another embodiment, the protective coating 104 is comprised of 9 layers. In some embodiments, the protective coating 104 is comprised of more than 9 layers.

In one embodiment, the protective coating 104 is comprised of an acrylate or mixture of acrylates. In some embodiments, the protective coating 104 is comprised of urethane acrylate, elastomeric urethane acrylate, aliphatic urethane acrylate, aliphatic urethane methacrylate, polycarbonate urethane acrylate, polycarbonate urethane methacrylate, epoxy acrylate, epoxy methacrylate, polyester acrylate, polyester methacrylate and/or oligomers of one or more of those materials. The specific percentage of acrylate by weight of the protective coating formulation used may be approximately 20% to approximately 80%. The specific percentage of acrylate by weight of the protective coating formulation used may be approximately 40% to approximately 60%. The specific percentage of acrylate by weight of the protective coating formulation used may be approximately 60% to approximately 80%. The specific percentage of acrylate may impact the desired final thickness of the protective coating in that the high percentages of acrylate result in a thicker protective coating. As used herein, the "protective coating formulation" may refer to the liquid state of the protective coating 104 before curing.

In one embodiment, the protective coating 104 is comprised of a multifunctional acrylate. In some embodiments, the protective coating 104 is comprised of difunctional acrylate. The protective coating 104 may comprise (a) an acrylate; (b) a photo-initiator comprised of an -benzophenone and/or hydroxyketone and (c) a solvent. The protective coating 104 may further include effective amounts of a (d) flow additive.

The protective coating 104 may also comprise one or more electromagnetic wave management materials and/or nanoparticles. The protective coating 104 may include a filter configured to limit the transmission of a laser through the optically transparent device. The protective coating 104 may include a filter configured to limit the absorption of light. The protective coating 104 may include a filter configured to control the transmission of specific electromagnetic wavelength bands.

In some embodiments, the protective coating formulation is comprised of a solvent or solvent mixture. The one or more solvents may comprise approximately 20% to approximately 80% by weight of the protective coating formulation. The one or more solvents may comprise approximately 20% to approximately 40% by weight of the protective coating formulation. The one or more solvents may comprise approximately 40% to approximately 60% by weight of the protective coating formulation. The amount of solvent used may depend on, among other things, the particular components employed to formulate the coating composition, the temperature of the coating composition, the coating thickness, and the coating technique to be used. A single solvent or a mixture of solvents may be used to dissolve acrylate and/or photo-initiator so that the coating composition can be readily applied. Solvents may include, for example, Isopropanol, 1-Methoxy-2-propanol and Ethyl Acetate, and mixtures thereof.

The formulation for protective coating 104 may comprise one or more flow additives. In one embodiment, the flow additives include one or more of dimethysiloxane and silicone containing surface additives (e.g., Tergitol 15-S-5, Tergitol TMN-3, Triton 57 and Triton X-100 from Dow Chemical Company, Dowsil™ 57 Additive, 205SL Additive and 401LS Additive from Dow Corning, BYK-361N, BYK 378 and BYK 3570, all from BYK-Chemie USA, Modaflow 9200 from Allnex and Tego Rad 2100 from Evonik Company.) Flow additives may be used to enhance the rheology of the coating formulation. The one or more flow additives present in the protective coating may range between approximately 0.01% to approximately 3% and from about 0.05% to 1% by weight of the protective coating formulation.

In one embodiment, the protective coating 104 contains a photoinitiator. The photo-initiator may be oligomeric polyfunctional alpha-hydroxyketone photoinitiator, 2-hydroxy-2-methyl-1-phenylpropanone, Benzophenone, or combinations thereof. Examples of a photoinitiator include, but are not limited to Chivacure 300 from Chitex Corporation, Omnirad 1173 (former Irgacure 1173 or Darocur 1173) and Ominpol BP from IGM resins USA Inc.

Figure 3:
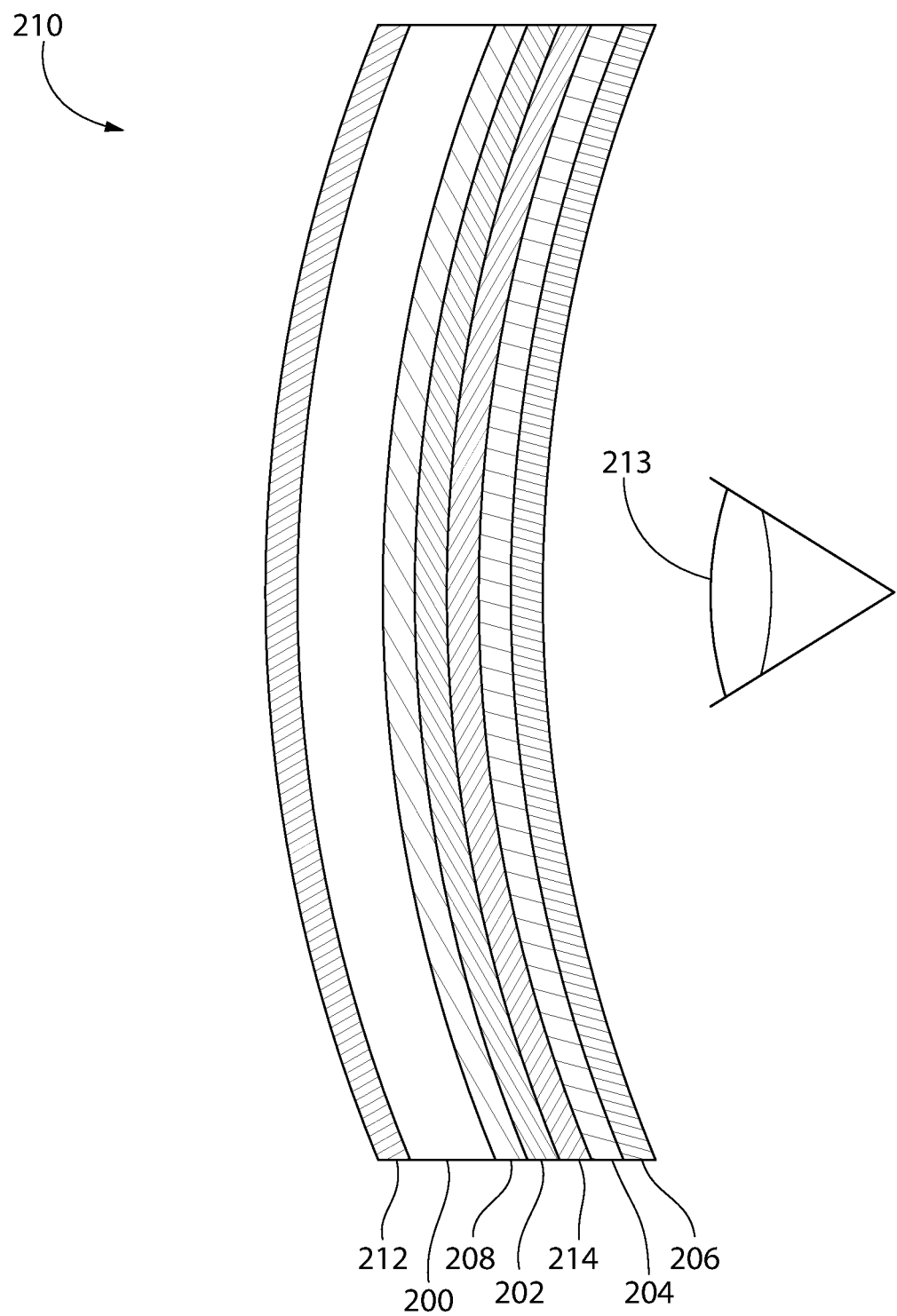
FIG. 3 is an enlarged partial side view of an optically transparent lens having an optical filter and a protective coating layer in accordance with another exemplary embodiment of the present invention.

Referring to FIG. 3, there is shown a second exemplary embodiment of the present invention. Various embodiments of the optical device 210 are described in further detail below in reference to the exemplary embodiments shown in the figures. One or more of the embodiments discussed in reference to the optical device 210 described below may be combined with one or more desirable features of the embodiments discussed in reference to the optical device 110 described above. In some embodiments, the optically transparent device 210 includes (a) an exterior lens 200, for example a polycarbonate spectacle lens that may or may not include light absorbing material incorporated into the exterior lens 200. In one embodiment, the exterior lens 200 may include a filter configured to limit the transmission of a laser. In another embodiment, exterior lens 200 may include a filter configured to limit the transmission of other wavelengths of light through the optically transparent device 210. In one embodiment, the exterior lens 200 comprises a concave surface configured to face toward a user 213, and a convex surface configured to face away from user 213, each of the concave and convex surfaces being coated with an abrasion resistant coating 208 and 212, respectively. In one embodiment, the optically transparent device 210 also includes an optical filter 202 coupled to the concave surface, an adhesion primer 214 coupled to the optical filter 202, and a protective coating 204 coupled to the adhesion primer 214. The optically transparent device may also include an anti-soil, anti-smudge, scratch resistant, hydrophobic, hydrophilic, anti-reflective and/or anti-fog coating 206 coupled to the protective coating 204. In some embodiments, optical filter 202 is situated between and is in direct contact with abrasion resistant coating 208 and adhesion primer 214.

The protective coating 204 may be a radiation curable coating. The protective coating 204 may have similar embodiments as described above for protective coating 104. In some examples, protective coating 204 includes one or more of: multifunctional acrylate, difunctional acrylate, monofunctional acrylate, urethane acrylate, elastomeric urethane acrylate, aliphatic urethane acrylate, aliphatic urethane methacrylate, polycarbonate urethane acrylate, polycarbonate urethane methacrylate, epoxy acrylate, epoxy methacrylate, polyester acrylate, polyester methacrylate and/or oligomers of one or more of those materials. The protective coating 204 may be comprised of a polymer with a thickness of approximately 2 microns to approximately 100 microns. In one embodiment, the formulation for protective coating 204 is comprised of approximately 20% to approximately 80% of aliphatic urethane acrylate by weight of the protective coating formulation. The specific percentage of acrylate by weight of the protective coating formulation used may be approximately 40% to approximately 60%. The specific percentage of acrylate by weight of the protective coating formulation used may be approximately 60% to approximately 80. The specific percentage of acrylate may impact the desired final thickness of the protective coating in that a higher percentages of acrylate may result in a thicker protective coating 204. Protective coating 204 may also include a photoinitiator. In one embodiment, the formulation for protective coating 204 also includes a solvent or solvent mixture. In one embodiment, the solvent mixture is approximately 20% to approximately 80% of the protective coating formulation. The one or more solvents may comprise approximately 20% to approximately 40% by weight of the protective coating formulation. The one or more solvents may comprise approximately 40% to approximately 60% by weight of the protective coating formulation. The protective coating 204 may also include one or more flow additives. Flow additives may include non-ionic, dimethysiloxane and/or silicone containing surface additives. In some embodiments, the one or more flow additives are between approximately 0.01% to approximately 3% by weight of the optical coating formulation for the protective coating 204.

In one embodiment, the method of preparing a lens having an optical filter 202 and a protective coating 204 includes providing an optically transparent substrate (e.g., a polycarbonate spectacle lens that may or may not include light absorbing material incorporated into the lens). In some embodiments, after providing optically transparent substrate, an optical filter 202 is coupled to the optically transparent substrate. In some embodiments, after coupling an optical filter 202, a primer layer 214 is applied to the optical filter 202. A primer layer 214 may be applied to a lint free, dry cloth and then wiped onto the optical filter 202. The primer layer 214 may alternatively be applied through dip, spin, flow or spray coating methods, onto the optical filter 202. The primer layer 214 may be dried. In one embodiment, a solvent based glass primer typically used for ultraviolet ink printing may be used as the primer layer 214. After the primer layer 214 is dried, the protective coating 204 may be applied. In one embodiment, coating methods may include dip, spin, flow or spray coating methods. Spin coating may be used in certain embodiments due to resulting uniformity of film coating. After applying protective coating 204, the protective coating 204 may be cured. In one embodiment, the concave and convex surfaces of the exterior lens 200 are coated with abrasion resistant coating 208 and abrasion resistant coating 212, respectively. In one embodiment, the protective coating 204 is cured by plasma arc discharges and/or mercury vapor lamps. The protective coating 204 may be cured with a total ultra violet ("UV") dosage from approximately 0.4 J/cm$^2$ to approximately 1.2 J/cm$^2$. In one embodiment, the source of UV irradiation may be a Fusion 300 H lamp. In one embodiment, after applying and curing the protective coating 204, an anti-reflective coating 206 or anti-fog coating is applied to the protective coating 204.

After forming the lens, the effectiveness of the protective coating to contain fragments or spall from a damaged optical filter, and remain attached to the optical device 210 or window, may be tested using common impact or ballistic methods including ANSI Z87.1 or MIL-STD662F, as appropriate for the designed service application.

Figure 4:
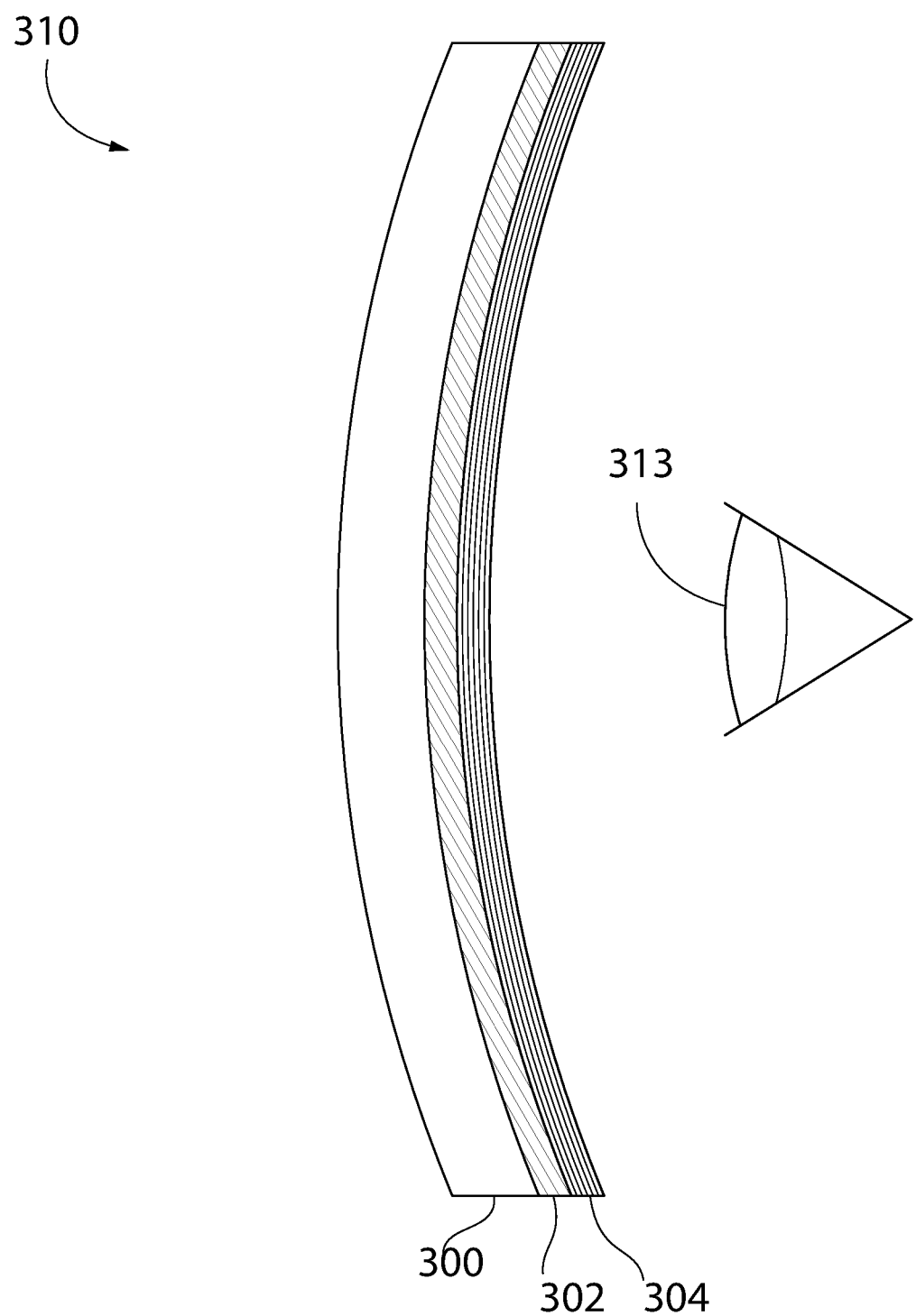
FIG. 4 is an enlarged partial side view of an optically transparent lens having an optical filter and a protective coating layer in accordance with another exemplary embodiment of the present invention.

Referring to FIG. 4, there is shown a third exemplary embodiment of the present invention. Various embodiments of the optical device 310 are described in further detail below in reference to the exemplary embodiment shown in the figures. One or more of the embodiments discussed in reference to the optical device 310 described below may be combined with one or more desirable features of the embodiments discussed in reference to the optical device 210 and/or optical device 110 described above. In one embodiment there is an optically transparent device 310 which includes an exterior lens 300, an optical filter 302 coupled to an inner surface of the exterior lens 300, and a protective coating 304 configured to face toward a user 313 and coupled to an inner surface of the optical filter 302. In one embodiment, the protective coating 304 may be made up of an aggregate of thin, multiple layers. In one embodiment, optically transparent device 310 does not include an interior lens. In one embodiment, optically transparent device 310 includes a single lens 300. In one embodiment, optical filter 302 is not positioned between two lenses. In some embodiments, optical filter 302 is situated between and is in direct contact with the inner surface of the exterior lens 300.

EXPERIMENTAL

Example 1

Substrate: a hard-coated polycarbonate lens with a multilayer dielectric optical filter on the concave side of the lens.

Primer: A solvent based glass primer typically used for UV ink printing was used for surface pretreatment prior to the application of the protective coating. On the concave side of the lens, apply primer to a lint free, dry cloth and wipe onto the substrate to be coated. Cover the entire substrate with a very thin uniform film. Wait for the primer to dry thoroughly at 20-25 C.

Protective coating formulation: The coating composition of Example 1 was prepared by initially dissolving 32.67 g of aliphatic urethane diacrylate in 32.67 g Isopropanol and mixing for 2 hours. Thereafter, 1.33 g Chivacure 300, an oligomeric polyfunctional alpha-hydroxyketone photoinitiator, was dissolved in 33.40 g Isopropanol and then added to the mixture. The mixture was mixed for another hour.

Protective coating application: The protective coating was applied via spin coating method on the concave side of the lens. The coating was cured with a 300 wpi Mercury Vapor Curing Lamp under ambient condition. The total UV dosage to cure the coating is about 0.8 J/cm$^2$. A transparent coating with about 7.4 microns thick was obtained.

Testing: A sample lens was tested using a cross hatch adhesion test and passed. Another sample from this experiment was subjected to an impact event using a 0.25 inch diameter steel ball shot at 250 feet/second as outlined in ANSI Z87.1. The protective coating stayed attached to the lens and contained all of the spall fragments from the damaged optical filter.

Example 2

Substrate: a hard-coated polycarbonate lens with a multilayer dielectric optical filter on the concave side of the lens.

Primer: Same as Example 1.

Protective coating formulation: Same as Example 1.

Protective coating application: The protective coating was applied via spin coating method on the concave side of the lens. The coating was cured with a 300 wpi Mercury Vapor Curing Lamp under ambient condition. The total UV dosage to cure the coating is about 0.8 J/cm$^2$.

Repeat protective coating application and curing steps for two more times resulting in a three-layer protective coating system with a total thickness of about 21.0 microns.

Testing: A sample lens was tested using a cross hatch adhesion test and passed. Another sample from this experiment was subjected to an impact event using a 0.25 inch diameter steel ball shot at 250 feet/second as outlined in ANSI Z87.1. The protective coating stayed attached to the lens and contained all of the spall fragments from the damaged optical filter.

Example 3

Substrate: a hard-coated polycarbonate lens with a multilayer dielectric optical filter on the concave side of the lens.

Primer: Same as Example 1.

Protective coating formulation: Same as Example 1.

Protective coating application: The protective coating was applied via spin coating method on the concave side of the lens. The coating was cured with a 300 wpi Mercury Vapor Curing Lamp under ambient condition. The total UV dosage to cure the coating is about 0.8 J/cm$^2$.

Repeat protective coating application and curing steps for 5 more times resulting in a six layer protective coating system with a total thickness of about 42.0 microns.

Testing: A sample lens was tested using a cross hatch adhesion test and passed. Another sample from this experiment was subjected to an impact event using a 0.25 inch diameter steel ball shot at 250 feet/second as outlined in ANSI Z87.1. The protective coating stayed attached to the lens and contained all of the spall fragments from the damaged optical filter.

Example 4

Substrate: a hard-coated polycarbonate lens with a multilayer dielectric optical filter on the concave side of the lens.

Primer: Same as Example 1.

Protective coating formulation: The coating composition Examples 2 was prepared by initially dissolving 39.2 g of aliphatic urethane diacrylate in 39.2 g 1-Methoxy-2-Propanol and mixing for 2 hours. Thereafter, 1.6 g Chivacure 300 was dissolved in 10.0 g 1-Methoxy-2-Propanol and then added to the mixture. 0.34 g of Dowsil™ 57 Additive, a non-reactive silicone glycol copolymer surfactant, was dissolved in 9.66 g Isopropanol and then added to the mixture. The mixture was mixed for another hour.

Protective coating application: The protective coating was applied via spin coating method on the concave side of the lens. The coating was cured with a 300 wpi Mercury Vapor Curing Lamp under ambient condition. The total UV dosage to cure the coating is about 0.8 J/cm$^2$. A transparent coating with about 7.3 microns thick was obtained.

Testing: A sample lens was tested using a cross hatch adhesion test and passed. Another sample from this experiment was subjected to an impact event using a 0.25 inch diameter steel ball shot at 150 feet/second as outlined in ANSI Z87.1. The protective coating stayed attached to the lens and contained all of the spall fragments from the damaged optical filter.

Example 5

Substrate: a hard-coated polycarbonate lens with a multilayer dielectric optical filter on the concave side of the lens.

Primer: Same as Example 1.

Protective coating formulation: The coating composition Examples 2 was prepared by initially dissolving 75.0 g of an elastomeric urethane acrylate in 21.0 g 1-Methoxy-2-Propanol and mixing for 2 hours. Thereafter, 2.0 g Omnirad BP, a benzophenone photoinitiator, and 2.0 g Irgacure 1173, a hydroxy phenyl propanone photoinitiator, were added and the mixture was mixed for another hour.

Protective coating application: The protective coating was applied via spin coating method on the concave side of the lens. The coating was cured with a 300 wpi Mercury Vapor Curing Lamp under ambient condition. The total UV dosage to cure the coating is about 1.2 J/cm$^2$. A transparent coating with about 42 microns thick was obtained.

Testing: A sample lens was tested using a cross hatch adhesion test and passed. Another sample from this experiment was subjected to an impact event using a 0.25 inch diameter steel ball shot at 150 feet/second as outlined in ANSI Z87.1. The protective coating stayed attached to the lens and contained all of the span fragments from the damaged optical filter.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. The words "right", "left", "lower" and "upper" designate directions in the drawings to which reference is made. The words "inwardly" and "outwardly" refer to directions toward and away from, respectively, the geometric center of the protective transparent coating for thin film optical filters. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also include a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. An optically transparent device comprising:
    an exterior lens comprised of:
        a concave surface configured to face toward a user, and a convex surface configured to face away from a user, each of the concave and convex surfaces being coated with an abrasion resistant coating; and
    a dielectric optical filter coupled to the concave surface;
    an adhesion primer coupled to the dielectric optical filter;
    a protective acrylate coating coupled to the adhesion primer wherein the protective acrylate coating has a thickness of approximately 5 microns to approximately 50 microns; and
    an anti-reflective and/or anti-fog coating coupled to the protective acrylate coating.

2. The optically transparent device of claim 1, wherein the protective acrylate coating is comprised of approximately 20% to approximately 80% of acrylate by weight of a coating formulation, and further comprises:
    a photo-initiator;
    a solvent mixture comprised of one or more solvents comprising: approximately 20% to approximately 80% by weight of the coating formulation;
    one or more flow additives comprised of:
        non-ionic, dimethysiloxane and/or silicone containing surface additives;
        wherein the one or more flow additives are between approximately 0.01% to approximately 3% by weight of the protective acrylate coating formulation,
    wherein the thickness of the protective acrylate coating is between approximately 2 microns to approximately 100 microns.

3. A method for manufacturing an optically transparent device comprising the steps of:
    providing an optically transparent substrate;
    coupling an optical filter to the optically transparent substrate;
    applying a primer layer to a lint free, dry cloth and then wiping the primer layer onto the optical filter;
    applying a protective coating to the optical filter; and
    curing the protective coating by radiation.

4. The method of claim 3, further comprising the step of:
    drying the primer layer before applying the protective coating to the optical filter.

5. The method of claim 3, wherein applying the protective coating to the optical filter includes flowing, spinning, dipping and/or spraying the protective coating onto the optical filter.

6. The method of claim 3, further comprising the step of:
    applying an anti-reflective, anti-fog, anti-soil, hydrophilic, hydrophobic and/or scratch resistant coating to the protective coating.

7. The method of claim 3, wherein curing the protective coating includes use of ultraviolet radiation.

8. The method of claim 3, wherein coupling the optical filter to the optically transparent substrate includes applying the optical filter using vacuum deposition technology.

9. The method of claim 3, wherein the optical filter is preformed to a general shape of the optically transparent substrate and subsequently bonded to the optically transparent substrate.

* * * * *